United States Patent [19]

Piccolo et al.

[11] Patent Number: 4,542,233

[45] Date of Patent: Sep. 17, 1985

[54] PROCESS FOR PREPARING BIARYL COMPOUNDS VIA COUPLING OF AN ARYLAMINE WITH AN ARENE

[75] Inventors: Oreste Piccolo, Leghorn; Aldo Belli, Cornate D'Adda; Giovanni Villa, Monticello; Enrico Zen, Macherio; Attilio Citterio, Monza, all of Italy

[73] Assignee: Biaschim S.p.A., Milan, Italy

[21] Appl. No.: 515,498

[22] Filed: Jul. 20, 1983

[30] Foreign Application Priority Data

Jul. 23, 1982 [IT] Italy .............................. 22554 A/82

[51] Int. Cl.[4] ................... C07C 67/343; C07C 45/69; C07C 51/353; C07C 120/00; C07C 37/14; C07C 76/02; C07C 41/18; C07C 148/00; C07C 17/26; C07C 2/68; C07C 2/69

[52] U.S. Cl. ................... 560/21; 260/465 D; 260/465 H; 560/9; 560/17; 560/51; 560/52; 560/54; 560/59; 560/81; 560/82; 562/431; 562/435; 562/460; 562/463; 562/469; 562/488; 568/58; 568/63; 568/66; 568/68; 568/306; 568/312; 568/315; 568/316; 568/424; 568/433; 568/585; 568/586; 568/631; 568/635; 568/636; 568/637

[58] Field of Search ................. 560/82, 81, 9, 17, 21, 560/51, 52, 54, 59; 585/427; 570/130, 183, 143; 568/811, 812, 924, 928, 931, 58, 66, 306, 63, 68, 312, 315, 316, 642, 306, 424, 433, 585, 586, 631, 635, 636, 637, 638, 639, 643, 707, 746, 747, 763, 765; 260/465 D, 465 M; 562/488, 435, 431, 460, 463, 469

[56] References Cited

U.S. PATENT DOCUMENTS

| | | | |
|---|---|---|---|
| 3,932,499 | 1/1976 | Adams et al. | 560/82 |
| 3,992,459 | 11/1976 | Utne | 585/427 |
| 4,052,514 | 10/1977 | Adams et al. | 560/82 X |
| 4,266,069 | 5/1981 | Walker | 560/20 |
| 4,324,904 | 4/1982 | Hylton et al. | 560/102 |

FOREIGN PATENT DOCUMENTS

| | | |
|---|---|---|
| 32620 | 7/1981 | European Pat. Off. |
| 2065655 | 7/1981 | United Kingdom |

Primary Examiner—Natalie Trousof
Assistant Examiner—Vera C. Clarke
Attorney, Agent, or Firm—Cushman, Darby & Cushman

[57] ABSTRACT

Improvement in the process for preparing biaryl compounds via coupling of an arylamine with an arene in the presence of a nitrite, an acid and copper metal or a derivative thereof; the improvement is consisting in adding to the reaction mixture a trialkylorthoformate. The process may be used for preparing drugs such as Flurbiprofen and Xenbucin or intermediate compounds particularly useful for preparing Flurbiprofen, Flufenisal, Chlordimorin, Xenbucin, Xenysalate, Xenyhexenic acid and the like.

15 Claims, No Drawings

PROCESS FOR PREPARING BIARYL COMPOUNDS VIA COUPLING OF AN ARYLAMINE WITH AN ARENE

This invention relates to an improvement in the process for preparing biaryl compounds via coupling of an arylamine with an arene in the presence of a nitrite, an acid and copper metal or a derivative thereof consisting in adding a trialkylorthoformate to the reaction mixture.

The U.S. Pat. No. 3,992,459 claims a process for improving the yields in biaryl compounds by reacting a benzenediazonium compound with a benzene compound in acid enviroment and in the presence of copper or a copper derivative.

The yields are insignificant when this process is used for preparing Diflunisal. Furthermore the yield of the biphenyl compound is about 65% when sodium nitrite is used (example 2 plus step B of the example 1) and the isolation of the benzene diazonium compound (example 2) is involved; this operation is very dangerous on industrial scale because of the poor stability and explosiveness of the diazonium salts. Better yields are attained when the process disclosed by U.S. Pat. No. 3,992,459 is carried out by using an alkyl nitrite instead of sodium nitrite. As a matter of fact it is known that the alkyl nitrites improve the yields but it is also known that they are very toxic, explosive and expensive.

The U.K. Patent Application No. 2,065,655 A discloses a process for preparing diphenyl compounds by coupling an aniline and a benzene in the presence of a metal nitrite; the yields range from 50 to 60% (examples from 1 to 9 and 11). Only in case of example 10 a yield of about 80% is declared. Better yields are attained by using alkyl nitrite which, however, show the above mentioned drawbacks.

Finally, the European Patent Application 32.620 discloses a process for preparing biphenyl compounds inclusive of Flurbiprofen; this process comprises many steps and one of these steps relates to the reaction of a substituted benzene diazonium compound with benzene. Also in this case the yields range, according to the working conditions, from 50 to 60% when it is used sodium nitrite (example 42) and from 50 to 70% when it is used an alkyl nitrite.

It has been now surprisingly found that the coupling yields of an arylamine with an arene in the presence of a nitrite and copper powder or a derivative thereof are substantially improved when a trialkylorthoformate is added to the reaction mixture. This finding is even more surprising and unexpected considering that the trialkylorthoformates are precursors of alcohols and that the alcohols promote the dediazoniation of diazonium salts (Angew. Chem. Int. ed., 17, 146, 1978). This improvement in the yields is particularly important when the reaction is carried out in the presence of a metal nitrite because it allows to attain yields that are comparable or better than those attainable with an alkyl nitrite without any of the drawbacks coming from the use of an alkyl nitrite.

The process according to this invention allows to prepare biaryl compounds according to the following scheme:

$$(R)_x ArNH_2 + (R')_y Ar'H \rightarrow (R)_x Ar-Ar'(R')_y \qquad (I)$$

wherein

Ar and Ar' are independently selected from aromatic and heteroaromatic radical;
x and y are independently selected from 0, 1, 2 and 3;
R and R' are independently selected from C 1-6 alkyl, substituted alkyl, cycloalkyl, substituted cycloalkyl, halogen, nitro, cyano, OZ, SZ, COZ, —O—COZ, $(NC)_m CB_p$, $(AOOC)_m-CB_p$, $(NC)(AOOC)CB_p$, COOZ
where
Z is hydrogen, C 1-6 alkyl, substituted alkyl, cycloalkyl, substituted cycloalkyl;
m is 1 or 2;
p is 2 when m is 1 and 1 when m is 2;
each B is independently selected from hydrogen, C 1-6 alkyl, substituted alkyl, cycloalkyl, substituted cycloalkyl; and
each A is independently selected fro hydrogen, C 1-6 alkyl, substituted alkyl, cycloalkyl, trialkylsilyl or, when m is 2, both A may form a cycle.

It will be evident to the expert that the above mentioned reaction afford to one product or to a mixture of isomers according to the number and the position of the substituents R'.

In this specification by "substituted" alkyl and cycloalkyl there are meant all the possible substitutions with one or more simple or complex groups which are known to the expert as inert in the reaction working conditions; example of these groups are the haloalkyl, nitroalkyl, alkoxyalkyl, cycloalkyl-alkyl and alkyl-thioalkyl.

Preferred meanings are
phenyl for Ar and Ar';
0,1 and 2 for x and y;
halogen, nitro

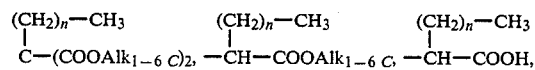

OH, $OAlk_{1-6C}$, $COAlk_{1-6C}$, $COOAlk_{1-6C}$, —O-$COAlk_{1-6C}$, (n being 0 or 1) for R and R'.

Some biaryl compounds of formula (I) are useful as drugs, such as Flurbiprofen and Xenbucin some others are particularly useful as intermediate compounds for preparing Flurbiprofen, Flufenisal, Diflunisal, Chlordimorin, Xenbucin, Xenysalate, Xenyhexenic acid and the like. The process according to this invention is carried out by adding the nitrite to the mixture of all the other reactants but the addition sequence of the various reactants may change case by case.

The acid may be inorganic such as the sulfuric, chloridric, fluoridric, methansulphonic and p-toluensulphonic acid, or organic such as the acetic, monohaloacetic, dihaloacetic, trihaloacetic (where the halogen may be fluorine, chlorine and bromine) or benzoic acid.

The nitrite may be either a metal nitrite or an alkyl nitrite.

The copper may be added in the form of a powder, an oxide, an organic or inorganic salt such as cuprous or cupric oxide, sulfate, halide and acetate.

An embodiment according to this invention comprises the addition of one mole of an arylamine, 1–1.5 moles of trichloroacetic acid, 0.001–0.1 moles of copper or of a derivative thereof and 1–5 moles of an trialkylorthoformate, to an excess with respect to the arylamine of the second aryl compound, which is so acting also as diluent of the reaction mixture. This excess being preferably of 10–100 moles.

The thus obtained mixture is brought to a temperature comprised between 20° C. and the boiling temperature of the reaction mixture, preferably from 40° to 80° C., and then 1–1.5 moles of the nitrite, preferably the sodium nitrite, are added.

The reaction is completed by keeping the reaction mixture under stirring at the above mentioned temperature for 1–40 hours.

The biaryl compound is isolated according to usual techniques.

Alternatively a mixture of the arylamine, trichloroacetic acid and trialkylorthoformate is added to a mixture of the nitrite and of copper or a derivative thereof in the second aryl compound.

The reaction is then carried out substantially as above described.

The above mentioned procedures are purely illustrative; as a matter of fact it will be possible to work according to any procedure known for preparing biaryl compounds via coupling of an arylamine with an arene in the presence of a nitrite and of metal copper or a copper derivative.

The improvement achieved by adding a trialkylorthoformate is consisting in an increase in yields which is comprised between 10 and 50% notwithstanding the diazo compound is not isolated.

Furthermore, the non-isolation of the diazocompound eliminates any risk of explosion and makes the process suitable for industrial working.

The following examples illustrate the process of this invention but are not to be construed as limiting.

EXAMPLE 1

2,4-difluorobiphenyl

A mixture of 2,4-difluoroaniline (3.52 g; 0.0273 mole), trichloroacetic acid (6 g; 0.0367 mole), cuprous chloride (0.14 g; 0.0014 mole) and of trimethylorthoformate (5.8 g; 0.0548 mole) in benzene (140.6 g; 1.8 moles) was heated to 60° C. under nitrogen.

Aliquots of sodium nitrite (2.1 g; 0.0304 mole) were added to the thus obtained mixture.

After having been kept under stirring for 16 hours, the reaction mixture was hydrolyzed with water and diluted hydrochloric acid. The organic layer was separated and washed with water till neutralization dried over sodium sulphate and concentrated. The residue was purified via chromatography on silica gel 60 (Merck 70-230 mesh) column; eluent, petroleum ether (40°–60° C.).

The solvent was removed and 4.7 g of 2,4-difluorobiphenyl melting at 63°–65° C. were thus obtained. Yield, 90%.

EXAMPLE 2

2,4-difluorobiphenyl

The procedure described in Example 1 was repeated without adding trimethylorthoformate; 3.5 g of the desired product were thus obtained. Yield, 67%.

EXAMPLE 3

2-fluorobiphenyl

The procedure described in Example 1 was repeated replacing 2,4-difluoroaniline with 2-fluoroaniline and continuing the stirring for 22 hours. After purification via chromatography on silica gel column, 4.7 g of 2-fluorobiphenyl melting at 74°–75° C. were obtained. Yield, 86%.

EXAMPLE 4

2-fluoro-4-bromo-biphenyl

The procedure in Example 1 was repeated replacing 2,4-difluoroaniline with 2-fluoro-4-bromoaniline. 4.0 g of 2-fluoro-4-bromobiphenyl were thus obtained, m.p. 36°–38° C. Yield, 83%

EXAMPLE 5

2(3'-fluoro-4'-phenyl)-phenyl-propionic acid

A mixture of 2-[(3'-fluoro-4'-amino)-phenyl]-propionic acid (5 g; 0.0273 mole), trichloroacetic acid (6 g; 0.0367 mole), cuprous chloride (0.14 g; 0.0014 mole) and of trimethylorthoformate (5.8 g; 0.0548 mole) in benzene (140.6 g; 1.8 moles) was heated to 60° C. under nitrogen.

To this mixture aliquots of sodium nitrite (2.1 g; 0.0304 mole) were added.

The reaction mixture was maintained under stirring for 26 hours and then hydrolyzed with water and diluted hydrochloric acid. The organic layer was separated and concentrated by evaporation of the solvent; the residue was treated with a 1:1 hydroalcoholic solution (200 ml) of 10% potassium hydrate and heated to reflux for two hours. After distillation of the solvent, the residue was taken up with water and the aqueous layer, after extraction with ethyl ether, was made acid with 10% hydrochloric acid. The organic compound was then extracted with ethyl ether and the organic layer washed with water till neutralization and dried over sodium sulfate. After removal of the solvent, the residue was chromatographed on silica gel 60 (Merck 70-230 mesh) column eluting with 9:1 benzene-acetone.

5.5 g of 2-[(3'-fluoro-4'-phenyl)-phenyl]-propionic acid were obtained; m.p. 111°–113° C. Yield, 82.6%.

EXAMPLE 6

2-[(3'-fluoro-4'-phenyl)-phenyl]-propionic acid

The procedure described in Example 5 was repeated without adding trimethylorthoformate; 2.4 g of the desired product were thus obtained. Yield, 36%.

EXAMPLE 7

Diethyl 2-methyl-2-(3'-fluoro-4'-phenyl)-phenyl-malonate

A mixture of diethyl 2-methyl-2-[(3'-fluoro-4'-amino)-phenyl]malonate (7.73 g; 0.0273 mole), trichloroacetic acid (5.5 g; 0.0336 mole), cuprous chloride (0.14 g; 0.0014 mole) and of trimethylorthoformate (6.8 g; 0.0637 mole) in benzene (140.6 g; 1.8 moles) was heated to 60° C. to the mixture aliquots of sodium nitrite (2.3 g; 0.033 mole) were added under stirring. The mixture was maintained under stirring for 43 hours at 60° C. and then hydrolyzed with water and diluted hydrochloric acid. The organic layer was separated, washed with water and concentrated. The residue was chromatographed on silica gel 60 (Merck 70-230 mesh) column eluting with 8:2 petroleum ether (40°–60° C.)/diethyl ether.

8.5 of diethyl 2-methyl-2-[(3'-fluoro-4'-phenyl)-phenyl]-malonate were obtained; m.p. 36°–38° C. Yield, 90%.

EXAMPLE 8

Diethyl 2-methyl-[(3'-fluoro-4'-phenyl)-phenyl]-malonate

The procedure described in Example 7 was repeated without adding trimethylorthoformate; 7.0 g of the desired product were thus obtained. Yield, 74%.

EXAMPLE 9

Methyl 2-[(3'-fluoro-4'-phenyl)-phenyl]-propionate

A mixture of methyl 2-[(3'-fluoro-4'-amino)-phenyl]-propionate (5.4 g; 0.0273 mole), trichloroacetic acid (5.5 g; 0.0336 mole), cuprous chloride (0.14 g; 0.0014 mole) and trimethylorthoformate (5.8 g; 0.0548 mole) in benzene (140.6 g; 1.8 moles) was heated to 60° C.

To the mixture aliquots of sodium nitrite (2.3 g; 0.0333 mole) were added under stirring. The mixture was maintained under stirring for 20 hours at 60° C. and then hydrolyzed with water and diluted at 60° C. and then hydrolyzed with water and diluted hydrochloric acid. The organic layer was separated, washed with water and concentrated. The residue was chromatographed on silica gel 60 (Merck 70-230 mesh) column eluting with 8:2 petroleum ether (40°-60° C.)/diethyl ether.

5.4 g of methyl 2-[(3'-fluoro-4'-phenyl)-phenyl]-propionate were obtained; m.p. 48° C. Yield, 78%.

EXAMPLE 10

Methyl 2-[(3'-fluoro-4'-phenyl)-phenyl]-propionate

The procedure described in Example 9 was repeated without adding trimethylorthoformate; 4.8 g of the desired product were thus obtained. Yield, 68,7%.

EXAMPLE 11

4-nitro-biphenyl

A mixture of 4-nitro-aniline (3.77 g; 0.0273 mole), trichloroacetic acid (6 g; 0.0367 mole), cuprous chloride (0.14 g; 0.0014 mole) and trimethylorthoformate (5.8 g; 0.0548 mole) in benzene (140.6 g; 1.8 mole) was heated to 60° C. Aliquots of sodium nitrite (2.3 g; 0.0333 mole) were added to the thus obtained mixture. The mixture was maintained under stirring for 22 hours at 60° C. and then hydrolyzed with water and diluted hydrochloric acid. The organic layer was separated, washed with water and concentrated. Crystallization of the residue from methanol afforded 5.8 g of 4-nitro-biphenyl, melting at 114°-116° C. Yield, 80%.

EXAMPLE 12

Diethyl 2-methyl-2-[(3'-fluoro-4'-phenyl)-phenyl]malonate

A mixture of diethyl 2-methyl-2[(3'-fluoro-4'-amino)-phenyl]malonate (85.7 g; 0.303 mole), trichloroacetic acid (61 g; 0.373 mole) and trimethyl orthoformate (75.4 g; 0.706 mole) was added slowly to a suspension of sodium nitrite (25.5 g; 0.366 mole) and cuprous chloride (3.1 g; 0.031 mole) in benzene (1600 g; 20.48 moles) at 60° C. The mixture was maintained under stirring for 30 hours at 60° C. and then hydrolyzed. By following the procedure of example 7, 93 g of diethyl 2-methyl-2-[(3'-fluoro-4'-phenyl)-phenyl]malonate were obtained. Yield, 89%.

We claim:

1. In a process for preparing biaryl compounds via coupling of an arylamine with an arene in the presence of a nitrite, an acid and metal copper or a derivative thereof according to the following scheme:

$$(R)_x ArNH_2 + (R')_y Ar'H \rightarrow (R)_x Ar-Ar'(R')_y \quad (I)$$

wherein
Ar and Ar' are independently aromatic radicals;
x and y are independently selected from 0,1,2 and 3;
R and R' are independently selected from C 1-6 alkyl, substituted alkyl, cycloalkyl, substituted cycloalkyl, halogen, nitro, cyano, OZ, SZ, COZ, —O—COZ, (NC)m CBp, (AOOC)m—CBp and (NC(AOOC)CBp,
where
Z is hydrogen, C 1-6 alkyl, substituted alkyl, cycloalkyl, substituted cycloalkyl or aryl;
m is 1 or 2;
p is 2 when m is 1 and 1 when m is 2;
each B is independently selected from hydrogen, C 1-6 alkyl, substituted alkyl, cycloalkyl and substituted cycloalkyl; and
each A is independently selected from hydrogen, C 1-6 alkyl, substituted alkyl, cycloalkyl and trialkylsilyl or, when m is 2, both A may form a cyclic ester;

the improvement comprising carrying out the reaction in the presence of a trialkylorthoformate.

2. Process according to claim 1, wherein Ar and Ar' are phenyl, x and y are independently selected from 0,1 and 2, R and R' are independently selected from halogen, nitro,

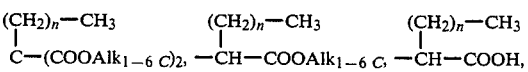

OH, OAlk$_{1-6C}$, —COAlk$_{1-6C}$, —COOAlk$_{1-6C}$ and —OCO Alk$_{1-6}$ (n being 0 or 1).

3. Process according to claim 1, wherein the trialkylorthoformate is trimethylorthoformate.

4. Process according to claim 1, wherein the reaction is carried out in the presence of trichloroacetic acid, sodium nitrite, cuprous halide and trimethylorthoformate.

5. Process according to claim 1, wherein 1 mole of an arylamine is coupled with an arene in the presence of 1-1.5 moles of trichloroacetic acid, 1-1.5 moles of sodium nitrite, 0,001-0,1 mole of cuprous chloride and 1-5 moles of trimethylorthoformate.

6. A process according to claim 2 wherein the trialkylorthoformate is trimethylorthoformate.

7. A process according to claim 2 wherein the reaction is carried out in the presence of trichloroacetic acid, sodium nitrite, cuprous halide and trimethylorthoformate.

8. A process according to claim 2 wherein 1 mole of an arylamine is coupled with an arene in the presence of 1-1.5 moles of trichloroacetic acid, 1-1.5 moles of sodium nitrite, 0.001-0.1 mole of cuprous chloride and 1-5 moles of trimethylorthoformate.

9. A process according to claim 1 wherein there is employed 1-5 moles of trimethylorthoformate.

10. A process according to claim 2 wherein there is employed 1-5 moles of trimethylorthoformate.

11. A process according to claim 10 wherein the arene is benzene.

12. A process according to claim 9 wherein the arene is benzene.

13. A process according to claim 8 wherein the arene is benzene.

14. A process according to claim 4 wherein the arene is benzene.

15. A process according to claim 1 wherein the arene is benzene.

* * * * *